United States Patent [19]

Tatum

[11] Patent Number: 5,457,832
[45] Date of Patent: Oct. 17, 1995

[54] CERVICAL PILLOW WITH VARIABLE THICKNESS HEAD AND NECK PORTIONS

[76] Inventor: Eugene T. Tatum, 1617 Euclid Ave., Bowling Green, Ky. 42103

[21] Appl. No.: 285,939
[22] Filed: Aug. 4, 1994
[51] Int. Cl.$^6$ ..................................................... A47C 7/36
[52] U.S. Cl. ................................................................ 5/636
[58] Field of Search .......................................... 5/636, 637

[56] References Cited

U.S. PATENT DOCUMENTS

| D. 214,302 | 6/1969 | Barber | 5/636 |
|---|---|---|---|
| D. 308,455 | 6/1990 | Jenney | 5/636 |
| 2,700,779 | 2/1955 | Tolkowsky | 5/636 |
| 2,940,088 | 6/1960 | Boos | 5/636 |
| 3,234,569 | 2/1966 | Stewart . | |
| 3,482,571 | 12/1969 | Behrendt | 5/636 |
| 3,574,397 | 4/1971 | Norriss . | |
| 3,667,074 | 6/1972 | Emery | 5/636 |
| 4,118,813 | 10/1978 | Armstrong . | |
| 4,129,029 | 3/1980 | Bond . | |
| 4,194,501 | 3/1980 | Watt . | |
| 4,218,792 | 8/1980 | Kogan | 5/636 |
| 4,349,925 | 9/1982 | Macomber . | |
| 4,424,599 | 1/1984 | Hannouche . | |
| 4,494,261 | 1/1985 | Morrow . | |
| 4,502,170 | 3/1985 | Morrow . | |
| 4,536,905 | 8/1985 | DeSantis . | |
| 4,550,458 | 11/1985 | Fiore . | |
| 4,550,459 | 11/1985 | Endel et al. . | |
| 4,748,702 | 7/1988 | Sandler . | |
| 4,773,107 | 9/1988 | Josefek | 5/636 |
| 4,777,678 | 10/1988 | Moore . | |
| 4,850,067 | 7/1989 | Latorre . | |
| 4,907,306 | 3/1990 | Nakaji . | |
| 4,928,335 | 5/1990 | Pedrow . | |
| 4,941,478 | 7/1990 | Takeuchi et al. . | |
| 5,014,377 | 5/1991 | Dixon . | |
| 5,016,303 | 5/1991 | Tanaka et al. . | |
| 5,018,231 | 5/1991 | Wang | 5/636 |
| 5,033,137 | 7/1991 | Pedrow . | |
| 5,038,432 | 8/1991 | Robillard et al. . | |
| 5,123,132 | 6/1992 | Dixon . | |
| 5,129,705 | 7/1992 | Wray | 5/636 |
| 5,214,814 | 6/1993 | Eremita et al. | 5/636 |

FOREIGN PATENT DOCUMENTS 2609616  7/1988  France ........................ 5/636

Primary Examiner—Michael J. Milano
Attorney, Agent, or Firm—Camoriano & Smith

[57] ABSTRACT

A U-shaped pillow provides for the maximization of the cross-sectional area of the air passage of the user at the level of the oropharynx. The user's head is extended backwards in the supine position with the natural curvature of the neck being supported by a supine neck resting portion and the user's occiput resting directly against the underlying mattress. Additionally the pillow has elevated lateral head and neck resting portions and sloped transitional neck resting portions, all structured so that when a user rolls between the supine and lateral decubitus positions the user's thoracic and cervical spine are maintained substantially aligned.

5 Claims, 3 Drawing Sheets

CERVICAL PILLOW WITH VARIABLE THICKNESS HEAD AND NECK PORTIONS

BACKGROUND OF THE INVENTION

It is estimated that nearly thirty million Americans suffer from some sort of sleep disorder. Frequently, the sleep disorder has a major impact upon the quality of life, manifesting itself in work absenteeism, reduction in the quality of work, injury on the job, marital stress, drug dependency, and various psychological disorders. The financial impact upon American business is staggering and is estimated to be greater than ten billion dollars annually.

One of the more common major sleep disorders is obstructive sleep apnea. In this affliction, there is episodic closure of the airway, resulting in the obstruction of breathing. Redundancy of mucous membranes, over-relaxation of pharyngeal muscles, and/or poor anatomical positioning of the head and neck appear to account for this phenomenon to varying degrees. When the airway is completely obstructed, the individual stops breathing for a period of time ranging from several seconds to several minutes. The struggle to breath becomes so frantic that the individual begins to wake up. This arousal from deep sleep results in a temporary reversal of the underlying sleep process so that the individual may take several gasping breaths before falling back into deeper sleep. This cycle may be repeated numerous times a night.

Under conditions where airway obstruction is incomplete, there is some passage of air, resulting in an unpleasant sound known as snoring created by the vibration of the relaxed mucous membranes. While the quality of sleep of snoring individuals may not be greatly affected, the quality of sleep of nearby individuals may be significantly and adversely affected. Moreover, a sizable number of people who snore do suffer from daytime somnolence or exhaustion, an indication of poor sleep quality.

There have been numerous attempts to eliminate or reduce obstructive sleep apnea or snoring through various pillow designs, with mixed results. One of the more successful approaches has been to incorporate a pillow feature which encourages the individual to extend the neck so that the cross-sectional area of the airway is increased. Features which encourage such anatomical positioning are described in various U.S. Patents such as U.S. Pat. Nos. 4,850,067; 5,014,377; and 5,123,132. Many of the pillow designs for elimination or reduction of obstructive sleep apnea or snoring employ tradeoffs between accomplishing this objective and comfort, using discomfort techniques to encourage the user to sleep in one position as opposed to another. Examples of these designs include U.S. Pat. Nos. 4,536,905 and 4,748,702. Still others restrict the movement of the user during sleep. Examples of these designs include U.S. Pat. Nos. 4,118,813 and 4,349,925. Various types of pillows have also been designed for orthopedic cervical support. These include U.S. Pat. Nos. 3,574,397; 4,424,599; 4,494,261; 4,550,458; 5,016,303; and 5,038,432.

It is an object of the present invention to provide a pillow structure that reduces the frequency and severity of obstructive sleep apnea or snoring, thereby improving the quality of sleep of the user and nearby individuals.

It is still another object of the present invention to provide a pillow structure that reduces the frequency and severity of obstructive sleep apnea or snoring without resorting to physical discomfort or restricting user mobility.

It is a further object of the present invention to provide a pillow structure that maximizes the cross-sectional area of the user's airway passage at the level of the oropharynx when the user is in a supine position, yet permitting the user to easily roll into the lateral decubitus position with the lateral side of the user's head abutting lateral side portions of the pillow.

It is yet another object of the present invention to reduce the potential for neck strain by providing for a pillow structure that places the cervical and thoracic spine of the user in substantially coextensive alignment in the supine and lateral decubitus positions and throughout the rolling movement between these positions.

Other objects of the present invention will become readily apparent to those skilled in the art from the following description and appended drawings wherein there is shown and described a preferred embodiment of the present invention.

SUMMARY OF THE INVENTION

A pillow in accordance with the present invention comprises a central, supine neck resting portion having a convexly curved upper surface and a width about equal to the length of a user's neck from the base of the skull to the base of the neck, a pair of elevated left and right lateral, neck resting portions having convexly curved upper surfaces, transitional portions having a curved upper surface connecting the lower central portion with the elevated left and right lateral neck resting portions, and a pair of substantially planar, headrest portions each connected to a respective lateral neck resting portion. The maximum compressed height and curvature of the neck resting central portion under the weight of the user, while lying supine, is such that the cervical spine is supported in its natural curvature, with the head and neck fully extended backwards (towards the mattress). This position maximizes the cross-sectional area of the air passage of the user at the level of the oropharynx. The height of the uncompressed transitional portion upper surfaces varies from a minimum about equal to the height of the uncompressed central portion upper surface and a maximum about equal to the height of the uncompressed lateral portion upper surfaces. The distance between the center line of the pillow and the juncture of the transitional portions and the respective connected lateral portions is less than or equal to the distance between the center line of the pillow and the lateral edge of the shoulder of a user lying in a supine position. Additionally, the height of the uncompressed lateral neck resting portions is about equal to the height of the user's cervical spine above the underlying mattress when the user assumes a side-resting or lateral decubitus position. These structural limitations ensure that the user, when rolling from a supine position to a lateral decubitus position, is able to position the lateral side of his or her head against one of the lateral headrest portions and to have his or her cervical spine in substantially coextensive alignment with his or her thoracic spine throughout the entire rolling motion.

As it will be realized, the invention is capable of other and different embodiments, including one which incorporates a thin, substantially planar, supine headrest portion. These embodiments are capable of modifications in various, obvious aspects, all without departing from the invention. Accordingly, the drawings and descriptions will be regarded as illustrative in nature and not as restrictive.

DETAILED DESCRIPTION OF THE PREFERRED EMBODIMENT

Figure 1:
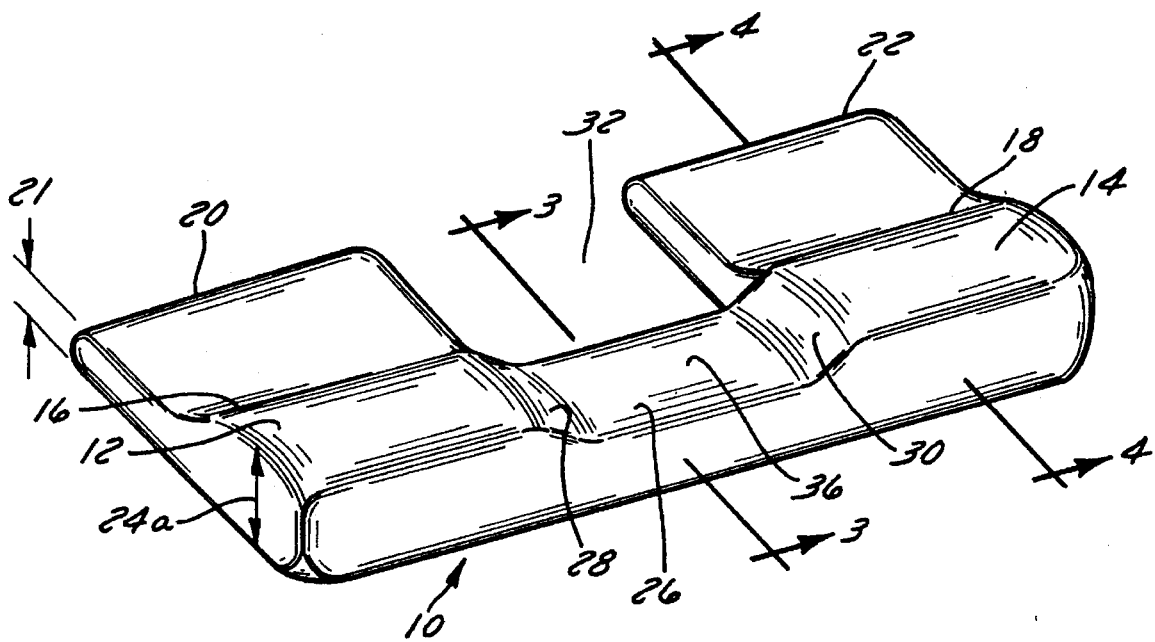
FIG. 1 is an oblique perspective of a pillow construction in accordance with the present invention.

Reference is first made to the perspective of FIG. 1 in which character numeral 10 refers to a pillow having a generally U-shaped configuration with sections or portions of various heights and curvatures. The composition of the pillow is preferably a soft, compressible material having a resiliency sufficient for the pillow depressed at any location by the user's head or neck to return to its original shape after the pressure has been released. Compositions suitable for use can include, but are not limited to, any foams selected from the family of polyurethane or polyolefin foams, preferably open celled foams with a compression deflection of about 0.5 to 2.0 inches downward displacement for a foam thickness of 4 to 6 inches due to a weight of about 10 pounds. In terms of ILD resiliency values, the expected range is 3 to 30 ILD, with preferred values generally from 10 to 20 ILD. ILD is a standard unit of measurement used for resiliency or firmness, frequently employed in the manufacture of pillows. See, for example, U.S. Pat. No. 5,128,132 issued Jun. 23, 1992 to Linda H. Dixon. An ILD value of 10 means that a 10 pound weight would displace a surface of a four inch thick piece of foam material by one inch. The major characteristic of the foamed material with respect to deflection compression is density. Foamed materials can be manufactured at about any density desired. Thus, the important aspect of the present invention is to select a density or densities that provide the various compression deflections desired. As discussed below, a proper compression deflection is needed to ensure that the correct anatomical positions of the user are maintained in order to promote restful sleep. Open celled foams are preferred due to their ability to repeatedly spring back into their original shape with minimal cell breakdown.

Pillow 10 is provided with elevated left and right lateral neck resting portions 12, 14 each with a convexly curved upper surface 16 and 18, respectively. For the adult user, the vertical height 24 of uncompressed portions 12, 14 is preferably about 4 to 8 inches, or approximately the width of the user's shoulder. Curved upper surfaces 16, 18 have a curvature which is complimentary to the lateral curvature of a user's neck from the top of the shoulder to the base of the head of the user. A preferred range of radii of curvature of upper surfaces 16, 18 is about 2 to 4 inches. Extending outward from the lateral neck resting portions are substantially planar left and right lateral headrest portions 20 and 22. Generally, the vertical height denoted by line 21 of portions 20 and 22 can range from a vertical height about equal to the vertical height of portions 12 and 14 to a vertical height that is substantially less. Preferably the vertical height of uncompressed portions 20, 22 is about 3 to 7 inches. The vertical height of the head and neck resting portions will necessarily vary somewhat, depending upon the head, neck and shoulder dimensions of the user and compressibility of the pillow and underlying body support structure or mattress.

Figure 4:
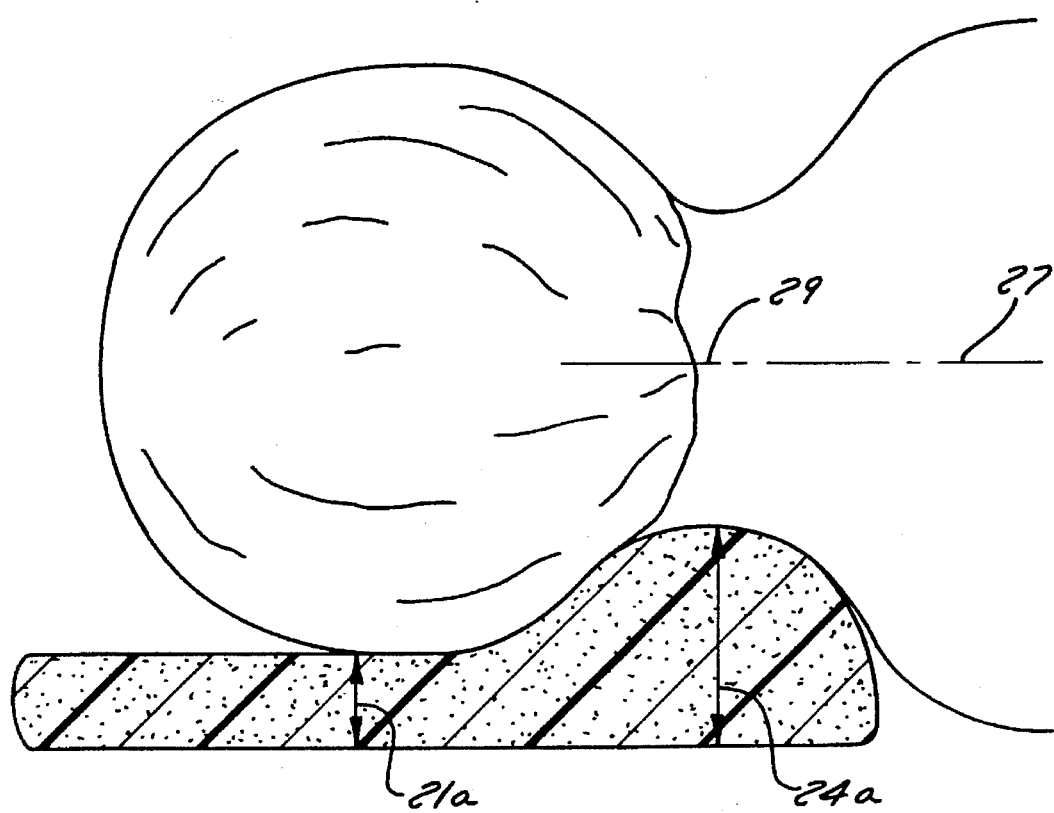
FIG. 4 is a sectional view of a pillow construction in accordance with the present invention taken along lines 4—4 of FIG. 1.

When, as shown in FIG. 4, the lateral side of a user's neck is resting against curved surfaces 16 or 18 and the lateral side of the user's head is lying against the corresponding lateral headrest portion 20 or 22, the vertical heights of the compressed lateral neck resting portion, denoted by line 24a, and the compressed lateral headrest portion, denoted by line 21a, should be such that the cervical spine 27 of the user is maintained in substantially "coextensive alignment" with the thoracic spine 29 of the user. The human spinal column has natural curvatures to the cervical and thoracic regions. As set forth in U.S. Pat. No. 4,494,261, the position of the body providing the natural curvature is termed the "physiologic" position. In the context of this description, the use of "coextensive alignment" should be understood to be synonymous with this "physiologic" position. Operationally, coextensive alignment exists when an imaginary line passing through the foramina of the T1 and C7 vertebrae extends also through the foramen of the C1 vertebra. A typical vertical height of compressed lateral neck resting portions needed to maintain an average-sized adult's spine in this substantially coextensive alignment is about 3 to 6 inches, while a typical vertical height of the compressed lateral headrest portions is about 2 to 5 inches. It is important that the vertical heights of the compressed lateral headrest and neck resting portions be properly selected to ensure the substantially coextensive alignment of the cervical and thoracic spine. Thus, the compressed vertical height 24a should be selected to correspond to a distance about one inch less than the width of the user's shoulder, as measured from the lateral edge thereof to the lateral edge of the user's neck. Similarly, the compressed vertical height 21a should be selected to correspond to a distance about one inch less than the distance from the lateral edge of the user's head to the level of the lateral edge of his shoulder when cervical spine 29 is in substantially coextensive alignment with thoracic spine 27.

Figure 5:
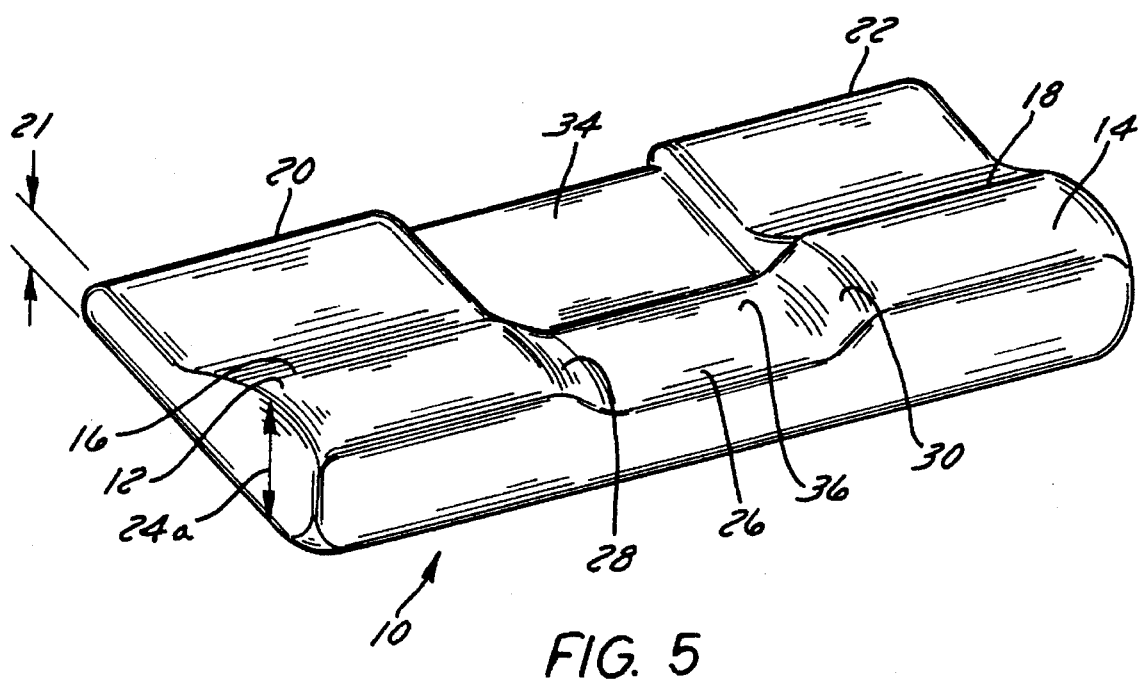
FIG. 5 is a perspective of an alternative pillow construction in accordance with the present invention.

Positioned between left and right lateral portions 12, 14 is a central supine neck resting portion 26 connected to the lateral portions by left and right transitional neck resting portions 28, 30. As can be seen from FIG. 1, pillow 10 forms a U-shape about a center area 32. Center area 32 is preferably open, such that the back of the user's head (occiput), lying in the supine position, directly abuts an underlying supporting surface such as a mattress. Alternatively, as shown in FIG. 5, a planar pillow extension or supine headrest portion 34 of preferably minimal compressed thickness, i.e., about one inch or less, may be used extending between the left and right lateral portions 12, 14 and central portion 26. Supine headrest portion 34 may be made of a foamed material having a greater density than other pillow portions so as to help maintain the integrity of the pillow when being handled. Additionally, supine headrest portion 34 can facilitate covering pillow 10 with a pillow case by providing a rectangular section to pillow 10.

Central portion 26 has a convexly curved upper surface 36 to correspond with the natural curvature of the user's neck. Central portion 26 has an uncompressed height of about 1.5 to 4 inches and a compressed height (shown by line 36a) of about 1 to 3 inches. The compressed height is such that when the user is lying in a supine position with the back of the neck resting against surface 36 and the back of the head contacting area 32, the user's head and neck are fully extended. It has been found that this position is within the comfort zone of the user and provides for a maximum opening of the air passageway of the user at the level of the oropharynx. The curved upper surface 36 provides a complimentary shape for abutment against the curved surface of the user's neck. The preferred range of radii of curvature of the surface 36 is about 1 to 4 inches.

Transitional portions 28, 30 provide for an increasing vertical height from the lower central portion 26 to the elevated lateral neck resting portions 12, 14. The function of the transitional portions is to provide continuous neck support for a user when the user rolls between the supine position and the lateral decubitus position, while concurrently maintaining the substantially coextensive alignment between the cervical and thoracic spine.

Figure 2:
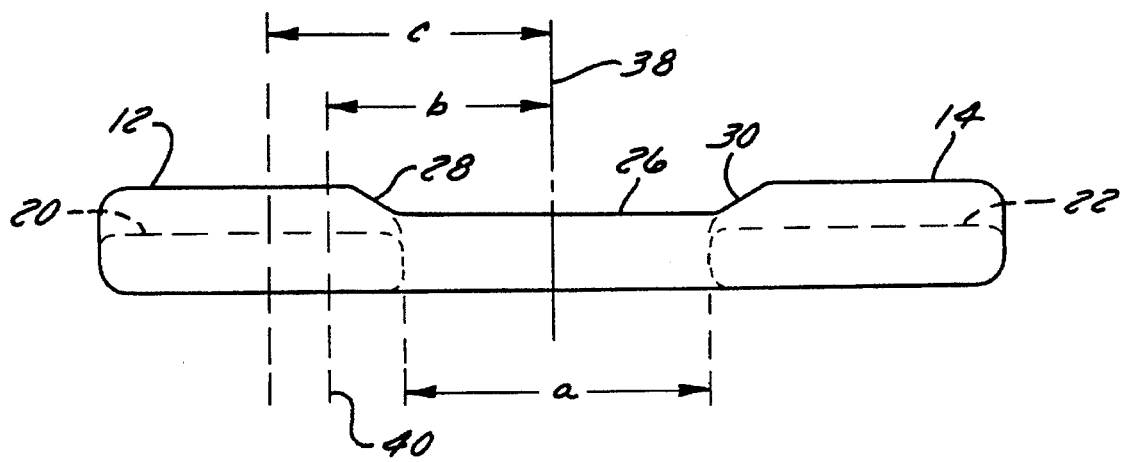
FIG. 2 is a front view of the pillow construction of FIG. 1.
Figure 3:
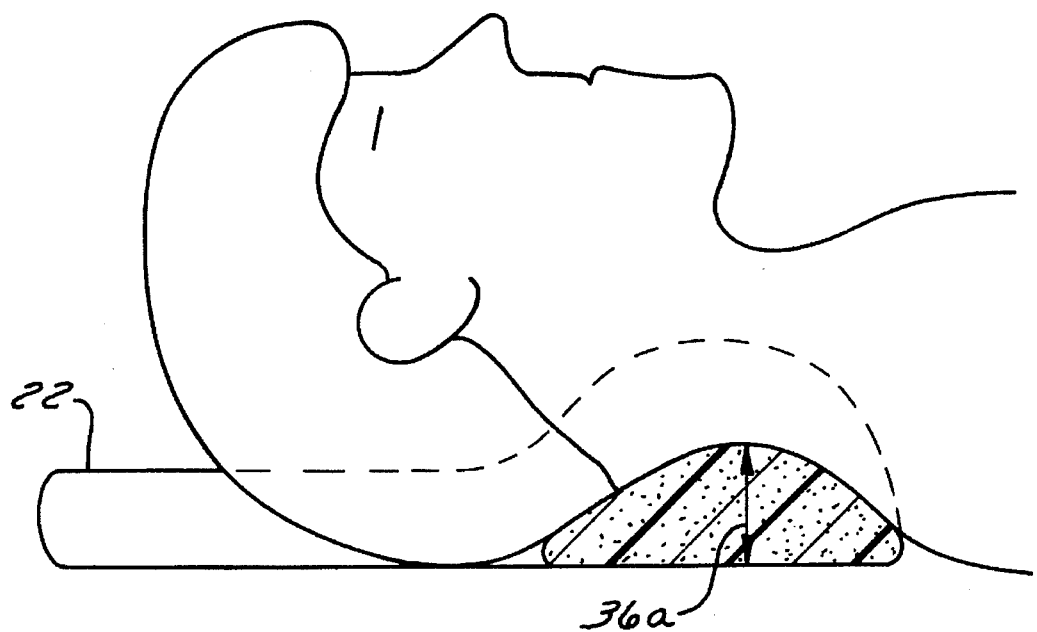
FIG. 3 is a sectional view of a pillow construction in accordance with the present invention taken along lines 3—3 of FIG. 1.

To ensure substantially coextensive alignment of the user's thoracic and cervical spine in the supine and lateral decubitus positions, and during the roll between the two positions, and to ensure maximization of the cross-sectional area of the user's air passage, it is necessary that certain pillow structure geometries be observed. First, as discussed above, a proper vertical height of the compressed lateral headrest and neck resting portions is required to ensure the substantially coextensive alignment when the user is in the lateral decubitus position. Second, a proper vertical height of the compressed central portion is necessary to promote user comfort and to maximize the cross-sectional area of the air passageway at the oropharynx level when the user is in the supine position. Finally, to ensure that the user's lateral neck side always rests against the lateral neck resting portion when the user has rolled into a lateral decubitus position, the rolling radius of a user must be equal to or slightly greater than the distance from the pillow center line to the transitional/lateral juncture. The rolling radius of the user is defined here to mean the distance from the lateral edge of the user's shoulder to the center line of the user. Generally, the user, as observed by inventor, will be more or less centered with respect to pillow 10 when lying in the supine position, thus meaning that the user's thoracic and cervical spine will be within the same plane as the center line of the pillow. Referring to FIG. 2, it may be seen that line "a" represents the length of supine neck resting portion 26. It is preferable that portion 26 have a length that approximates the width of a user's neck. Line "b" represents the distance from the center line 38 of the pillow and supine neck resting portion 26 to the juncture 40 between transitional portions 28, 30 and respective lateral neck resting portions 12, 14. Line "c" represents the rolling radius. It is important to note that transitional portions 28, 30 serve to provide support to the user's neck and to maintain the substantially coextensive alignment between the thoracic and cervical spine during the rolling movement between the supine and lateral decubitus positions.

In this disclosure, there is shown and described only the preferred embodiment of the invention, but it is understood that the invention is capable of changes and modifications within the scope of the inventive concept as expressed herein.

I claim:

1. A pillow for the reduction of neck strain, snoring and obstructive sleep apnea by maximizing the opening of a user's oropharynx and for maintaining the user's cervical spine and thoracic spine in substantially coextensive alignment throughout a rolling movement from a supine to a lateral position comprising (a) a pair of elevated left and right lateral neck resting portions each having a convexly curved upper surface with a predetermined uncompressed vertical height;

(b) a lower central supine neck resting portion lying between said elevated left and right lateral neck resting portions, said central portion having
a convexly curved upper surface adapted to be compressed into substantially continuous contact with the curved nape of a neck of said user lying in a supine position,
said upper surface having a maximum compressed vertical height and curvature under the weight of said user so that the natural curvature of said user's neck is maintained and the head and neck are fully extended backwards towards a mattress underlying said pillow and said user's occiput rests directly on the underlying mattress, thus maximizing the cross-sectional area of said user's oropharynx when in a supine position;

(c) a pair of neck resting transitional pillow portions connecting said neck resting central portion with said left and right neck resting lateral portions, said neck resting transitional pillow portions having upwardly sloping curved upper surfaces connecting said curved surface of said central neck resting portion with said curved surfaces of said left and right neck resting lateral portions, said curved upper surfaces of said left and right neck resting lateral portions having an uncompressed vertical height greater than an uncompressed vertical height of said neck resting central portion, and (d) a pair of lateral headrest portions each respectively connected to one of said left and right lateral neck resting portions, said lateral headrest portions defining the legs of a U-shaped pillow structure and said lateral, supine and transitional neck resting portions defining the bottom of said U-shaped pillow structure, said lateral headrest portions further being substantially planar and horizonal and having a maximum uncompressed vertical height less than said uncompressed vertical height of said curved surfaces of said left and right lateral neck resting portions so that said user's cervical spine is maintained in substantially coextensive alignment with the user's thoracic spine when said user's head laterally rests against the lateral head resting portions,
wherein a perpendicular distance measured from the center line of said pillow to the juncture between the lateral neck resting portions and the transitional portions is less than or equal to a distance measured from said center line to a lateral edge of said user's shoulder when lying in said supine position, thereby ensuring that when said user rolls from the supine position to a lateral position,
(i) the user's head pivots about an axis defined by a humerus of the user so that a lateral side of said user's head is positioned in an abutting relationship with one of said lateral headrest portions when said user is in a lateral decubitus position and
(ii) the neck of said user lies in substantially continuous abutment with the curved surface of one of said transitional portions and one of said left or right lateral neck resting portions, and
(iii) the user's cervical spine and thoracic spine are in substantially coextensive alignment throughout the rolling movement.

2. The pillow of claim 1 in which said compressed vertical height of said central supine neck resting portion is about 1 to 3 inches and said uncompressed vertical height of same is about 1.5 to 4 inches.

3. The pillow of claim 1 in which the user's neck compresses said lateral neck resting portions from an uncompressed vertical height of about 4 to 8 inches to a compressed vertical height of about 3 to 6 inches.

4. The pillow of claim 1 in which the user's neck compresses said lateral headrest portions from an uncompressed vertical height of about 3 to 7 inches to a compressed vertical height of about 2 to 5 inches.

5. The pillow of claim 1 in which said pillow has a resiliency allowing a depression of about 0.5 to 2 inches under a weight of about 10 pounds and springs back to its original uncompressed height after the weight is removed.

* * * * *